United States Patent [19]

Harris

[11] 3,937,826
[45] Feb. 10, 1976

[54] FLY KILLING COMPOSITION

[75] Inventor: Lewis P. Harris, Prairie Village, Kans.

[73] Assignee: PBI-Gordon Corporation, Kansas City, Kans.

[22] Filed: May 3, 1974

[21] Appl. No.: 466,781

Related U.S. Application Data

[63] Continuation-in-part of Ser. No. 359,767, May 14, 1973, abandoned.

[52] U.S. Cl. .................. 424/219; 424/17; 424/225
[51] Int. Cl.² ......................................... A01N 9/36
[58] Field of Search .......... 424/17, 19, 31, 219, 225

[56] References Cited
UNITED STATES PATENTS

| | | | |
|---|---|---|---|
| 3,074,845 | 1/1963 | Geary | 424/32 |
| 3,274,052 | 9/1960 | Yaffe et al. | 424/218 |
| 3,366,539 | 1/1968 | Woodbury | 424/218 |

OTHER PUBLICATIONS

*Science*, Vol. 40, No. 3574, pp. 1367–1373, (1963).
*Soap & Sanitary Chemicals*, Vol. 18, No. 4, pp. 97–99, 105 & 107, (1942).
Pesticide Index, Freak, p. 196, (1963).
*Modern Insecticides & World Food Prod.*, Gunther & Jeppson, P. 249, (1960).

*Primary Examiner*—Leonard Schenkman

[57] ABSTRACT

A fly killing composition in granular form characterized by synergistic attractant properties, an unusually long useful life, and substantial resistance to inactivation due to moisture. The composition comprises a combination base of granular, dark colored fly attractant such as fish food containing meat by-product material, in conjunction with a cooked, bright yellow, sugar-based attractant. These materials are coated with and absorb into the interstices thereof fly-toxic quantities of a mixture of 2,2-dichlorovinyl 0,0-dimethyl phosphate and 0,0-dimethyl 0-2,4,5-trichlorophenylphosphorothioate. A dusting powder applied to the insecticide impregnated particles assures that the surfaces thereof present a dull appearance notwithstanding the presence of a substantial amount of sugar in the bait formulation. The resultant fly killing composition is extremely effective in attracting flies thereto, and by virtue of the fact that the toxicants thereof are absorbed into the attractant base, the bait is not susceptible to moisture inactivation and flies alighting thereon are not repelled by the toxicant but rather are quickly killed thereby. The preferred method of use comprises spreading a thin layer of granular bait on the ground or other surface proximal to areas where flies tend to congregate, for example in dairy barns or poultry-keeping pens.

3 Claims, No Drawings

3,937,826

FLY KILLING COMPOSITION

CROSS REFERENCE

This is a continuation-in-part of copending application Ser. No. 359,767, filed May 14, 1973 now abandoned and entitled FLY KILLING COMPOSITION. The common subject matter of the parent application is expressely incorporated by reference herein.

BACKGROUND

This invention relates to a fly killing composition for use on the ground or other horizontal surfaces and which is especially useful in areas of high fly population such as dairy barns and poultry-keeping pens. More particularly, it is concerned with a composition that has improved fly attractant characteristics in conjunction with an unusually long useful life and is substantially impervious to the inactivating effects of moisture.

In the past, granular fly killing compositions for use in the areas described have comprised coarsely ground, granular sugar as an attractant base in conjunction with an insecticide coating thereover. Typical insecticides used in these formulations included 2,2-dichlorovinyl 0,0-dimethyl phosphate and 0,0-dimethyl 0-2,4,5-trichlorophenylphosphorothioate, each being used alone or in combination. The former is commonly referred to in the art as "DDVP", and the latter is referred to as "ronnel".

In practice however, the presently available fly killing compositions are deficient in several important respects. First, they generally exhibit only very short active fly-killing lives, which of course necessitates continual removal of spent bait and replacement thereof. For example, conventional granulated sugar based fly baits treated with DDVP alone are normally effective only for a period of about 48 hours, and even this time is lessened during extremely hot and humid weather. Similarly, a combination of DDVP and ronnel on granulated sugar usually has a maximum effective life of no longer than about 2 or 3 days. Lack of longevity is believed to be at least partly attributable to the fact that the toxicants are not significantly absorbed into the sugar attractant but reside on the surfaces of the crystals thereof and thus dissipate rather rapidly into the atmosphere, particularly during hot weather use when the pesticide is most sorely needed.

The effectiveness of these baits is further diminished because of the fact that moisture in the form of rainfall or the like serves to at least partially inactivate the composition because the sugar dissolves in rainwater and the granules either wash away or slowly disentegrate, causing rapid loss of the toxic agent. Hence, it is often necessary to replace these compositions after a rainfall because of the fact that they are no longer capable of killing flies.

Finally, some fly baits, particularly of the granulated sugar type which have only a surface coating of toxicant thereon have in fact repelled flies initially attracted thereto before the same could be killed. This is believed to occur at least in part because the shiny surfaces of the sugar granules repels the flies and the toxicant is relatively ineffective unless the insects directly contacted the active agent or are subjected to a lethal dose of the vapor thereof.

Hence, there is a great need in the art for an effective fly killing composition which attracts flies thereto without a subsequent repellent effect, is operative for an extended period of time, and can be employed without fear of rapid inactivation by virtue of adverse atmospheric conditions.

SUMMARY

The granular fly killing composition in accordance with the invention broadly comprise a major proportion of bright yellow, cooked, sugar-based attractant in conjunction with dark, highly absorptive meat-containing attractant granules interspersed therethrough. These granular base materials are treated with fly toxic quantities of 2,2-dichlorovinyl 0,0-dimethyl phosphate and 0,0-dimethyl 0-2,4,5-trichlorophenylphosphorothioate in order to thoroughly impregnate the same and effect at last partial absorption of the toxicant agents into the interstices of the base. A dusting powder applied to the treated granules renders the particles thereof of such dull appearance that there is no tendency for flies to be repelled from the bait because of shiny surface characteristics. The resultant final product is basically yellow in color with the dark meat-containing granules scattered throughout. This combination of colors has proven to be synergistically effective in attracting flies, and acc It is known that sufficiently dark granules can in some instances attract insects such as mosquitos by virtue of their appearance alone; however, in the development of the present invention it has been unexpectedly discovered that fly attraction is measurably enhanced when bright yellow, sugar-based fly attractant materials are incorporated therewith to form a less expensive combination attractant base of pleasing appearance to the user.

The bright yellow attractant base is preferably a mixture of sugar, corn syrup, corn grits and cereal, egg yolk and milk powders, vegetable oil and yellow food grade dye which are mixed, cooked and granulated into bits. In this connection, especially advantageous results are obtained by cooking the base in a continuous extrusion cooker followed by chopping or crushing in conventional apparatus to yield a free-flowing, irregular granular product. Coating of toxicant impregnated bits with a dry powder composition similar to the formula of the base bits increases the attractant properties of the base, not only with respect to house flies, but also other species of flies such as blow flies. This is a particularly desirable feature of the present invention, in that blow flies and similar species are not generally attracted to sugar baits.

The dark meat-containing component of the compositions hereof is likewise preferably an extrusion cooked, absorptive product which contains beef meat scraps and by-products, dried poultry by-products, and ground meals such as cottonseed, soybean, milo, wheat and dehydrated alfalfa.

It has also been found that through the use of appropriate quantities of the defined insecticides, the toxicants are rendered non-repellent to flies and give kills equivalent to relatively high levels of each when used alone. Therefore, it is possible to employ minimum amounts of each of the two insecticides, and when used with the attractant base described, a synergistic result is produced thereby.

A prime advantage of the fly killing compositions of the present invention results from the fact that they remain active for extremely long periods, both during storage and when in actual use. For example, a typical composition in accordance with the invention remains effective for up to seven days even under outdoor exposure conditions. Moreover, the composition is highly resistant to moisture inactivation from rainfall, and therefore can be employed in areas heretofore impossible to protect using prior fly killing compositions. The unexpectedly long useful life of the fly killing composition appears to be attributable to the fact that the organic matter thereof absorbs the active toxicant agents and very slowly releases the same over time substantially at the rate required for killing of flies exposed thereto. Most importantly, this effect obtains even after the composition has been on the ground for an extended period of time, for example two to three times longer than the effective fly killing lives of conventional sugar baits.

The method of use of the improved fly killing composition disclosed herein involves simply spreading a thin layer of the material in fly attracting dispostion. This can either be directly on the flooring of barns, or on the ground in livestock pens or the like where flies normally congregate.

DETAILED DESCRIPTION

As outlined above, it has been found that highly absorptive, dark colored, granular attractant base materials containing meat by-products such as beef scraps and by-products and dried poultry materials is especially effective as a fly attractant when used in conjunction with a bright yellow colored, cooked, sugar-based attractant. Although the meat by-products are believed to be the principal fly attractant agent in the dark granules, such materials can also be mixed with ground meals such as cottonseed, soybean, milo, wheat and dehydrated alfalfa and mixtures thereof to good effect. The following percentages of such components have been found to yield particularly efficacious dark attractant materials, when extruded or pelletized into a relatively coarse, granular state:

TABLE I

| | |
|---|---|
| Beef Scraps and By-Products | 15.00 – 20.00% |
| Dried Poultry By-Products | 10.00 – 15.00% |
| Cottonseed Meal | 15.00 – 20.00% |
| Soybean Meal | 10.00 – 15.00% |
| Pulverized Milo | 15.00 – 20.00% |
| Wheat Middlings | 1.00 – 5.00% |
| Dehydrated Alfalfa Meal | 10.00 – 15.00% |

(All percentages given by weight; remaining components, if any, are inert ingredients).

The above-defined dark attractant compositions also find utility as fish food for use in commercial-scale fish farming, and the components listed give exemplary fish food compositions. While such dark attractant granules can serve alone as a fly attractant, they are somewhat objectionable for several reasons. Specifically, such materials are relatively expensive to produce, especially when large quantities thereof are needed. Furthermore, the uniformly dark appearance thereof renders the resulting composition unattractive to the eye, and makes it difficult to discern the remains of flies killed thereby.

In this connection it has been found that an extremely effective fly attracting and killing composition can be produced by using as little as from 2 to 20% by weight of such fish food pellets, with the major proportion of the remainder of the composition (e.g., from about 70 to 90% by weight), being composed of a bright yellow, sugar-based product. For example, particularly effective bright yellow sugar-based attractants comprise the following:

TABLE II

| | |
|---|---|
| [1]Sugar | 40.00 – 60.00 |
| Corn Syrup | 10.00 – 15.00 |
| Corn Grits | 20.00 – 30.00 |
| Corn Cereal | 5.00 – 10.00 |
| Egg Yolk Powder | 0.01 – 0.10 |
| Milk Powder | 0.25 – 1.00 |
| Vegetable Oil | 1.00 – 5.00 |
| Yellow Food Grade Coloring | 0.15 – 0.50 |

[1] all data given in parts by weight

Following conventional extrusion cooking of the above mixture, the cooked product is cut and sized utilizing a standard rotary cracker or chopper and an 8 mesh screen, with the fines being separated out.

The dark and yellow attractant base materials described are then thoroughly admixed and subsequently sprayed with a mixture of 2,2-dichlorovinyl 0,0-dimethyl phosphate and 0,0-dimethyl 0-2,4,5-trichlorophenylphosphorothioate in order to produce an effective fly killing composition. This mixture is employed in an amount that is toxic to flies in proximity thereto but is not repellent to the insects. That is, it has been found that when excessive amounts of these insecticides are employed, an undesirable fly repellant effect can be produced. Additionally, amounts can be used which tend to diminish the "arrestant" effect of the composition. In such a case, flies will initially be attracted by the composition and commence to land or stay on the bait only momentarily and thereby not be subjected to a lethal dose of the toxic agents. By virtue of the use of an organic compressed material such as dark colored fish food for the principal attractant, the pesticide agents are only slowly and relatively uniformly released therefrom. This rate is not significantly affected even if it rains on the product since the water cannot readily wash the agents out of the interior cavities of the fish food granules.

Therefore, it is necessary to utilize the defined insecticide within the relatively narrow limits of practical use. In particular, it has been found that a mixture of from 0.10 to 3% 2,2-dichlorovinyl 0,0-dimethyl phosphate and from 0.25 to 2% of 0,0-dimethyl 0-2,4,5-trichlorophenylphosphorothioate is particularly advantageous, both percentages being by weight and based upon the total weight of the treated granules. In the most preferred form, DDVP is employed at a level of about 0.47 weight percent while ronnel is used at a level of about 0.54 weight percent, both toxicants being admixed in a minimum of methylene chloride or other suitable volatile solvent. As much as possible, the solvent employed is volatized during subsequent preparation procedures in order to minimize any repellent effects of the solvent itself and to "fix" the toxicants within the base therefor.

In the use of the preferred treated insecticide-treated attractant granules described above, it has also been found helpful to coat the latter with a dusting powder comprising finely ground, particulate composition containing dried milk, dried egg yolks, yellow food dye and a density controlling agent such as hydrated amorphous silica oxide. A coating using such a composition is most effectively applied to the base granules after the toxicant solution thereon has dried and absorbed into the interstices thereof to impart a dull surface appearance to the bait particles. The compositions can advantageously contain from 0–10% dried milk, from 0–5% dried egg yolks, 0.1–5% hydrated amorphous silica oxide and from 0–0.5% yellow dye, all percentages by weight based upon the total weight of the fly-killing composition.

The following example is given in order to illustrate the production of preferred fly killing composition in accordance with the invention, but the specifics thereof are not to be construed as limitations on the overall scope of the invention.

EXAMPLE

A dark, brown-black pelletized fish food composition containing the components listed below was prepared by admixing the various components and extruding the latter in a conventional cooker-extruder using steam and elevated pressures. The ingredients employed in the production of this fish food product are as follows:

TABLE III

| | | |
|---|---:|---|
| Cottonseed Meal | 15.50 | lbs. |
| Soybean Meal | 13.25 | |
| Pulverized Milo | 15.33 | |
| Dicalcium Phosphate | 3.77 | |
| Salt | 0.55 | |
| Vitamin Concentrate | 0.45 | |
| Wheat Middlings | 4.40 | |
| Dehydrated Alfalfa Meal | 10.00 | |
| Beef Scraps and By-Products | 18.50 | |
| Dried Poultry By-Products | 13.50 | |
| Molasses | 2.50 | |
| Bentonite | 1.25 | |
| Calcium Carbonate | 1.00 | |
| | 100.00 | lbs. |

Upon exiting from the extruder the cooked product was cut and sized through an 8 mesh screen in order to produce a granular, dark, absorptive organic fly attractant.

In like manner, the bright yellow, sugar based component of the composition was produced by extrusion-cooking methods. In particular, the following ingredients were intitially admixed and passed through a standard cooker-extruder under normal operating conditions of high temperature, pressure and shear:

TABLE IV

| | |
|---|---:|
| ¹Sugar | 52.00 |
| Corn Syrup | 12.00 |
| Corn Grits | 26.00 |
| Egg Yolk Powder | 0.06 |
| Milk Powder | 0.50 |
| Vegetable Oil | 2.00 |
| Yellow Dye (Food Grade) | 0.38 |

¹all data given in parts by weight

After cooking, the bright yellow product was sized by utilization of a conventional rotary chopper or cracker which employs a pair of rotating, slightly spaced rollers for sizing. Following chopping, the yellow granular material was passed through a vibrating 8 mesh screen whereupon the correctly sized granules were collected and the larger granules returned to the chopper for further treatment. Any fines carried with the 8 mesh granules were removed by screening the latter with a 20 mesh screen, whereupon the fines were returned for inclusion with the next batch.

The final fly killing composition comprised the following ingredients, all given on a weight percentage basis:

TABLE V

| | |
|---|---:|
| Yellow Sugar Base | 81.20% |
| Dark Fish Food Granules | 15.00% |
| 67% Ronnel (Dow Chemical Co.) | 0.80% |
| 93% DDVP (Shell Chemical Co.) | 0.50% |
| Beta Napthol (Stabilizer for DDVP) | 0.50% |
| Dried Milk Powder (Carnation Co.) | 1.50% |
| Dried Egg Yolk Powder | 0.25% |
| ¹Hisil(R) 233 | 0.22% |
| Yellow Brilliant Dye | 0.33% |
| | 100.00% |

¹Hydrated amorphous silica oxide sold by PPG Industries of Pittsburgh, Pennsylvania The above listed constituents were handled in the following manner. The completely cooled fish food and yellow sugar based granules were first introduced into a rotary barrel tumbler and thoroughly admixed. A previously prepared toxicant solution containing the DDVP, ronnel and beta napthol in a minimum of methylene chloride solvent was then sprayed onto the tumbling attractant base granules while mixing thereof continued. At this point the initial liquid toxicant solution was allowed to dry and absorb into the base materials for a period of at least about 10 minutes.

The treated base granules were then coated with a dry particulate mixture of the blended milk, egg yolks, silica oxide and dye while tumbling was continued for about 10 minutes. The resulting finished granular product was generally bright yellow in color with partially coated brown-black fish food pellets interspersed throughout.

Additionally, it should be noted that the residual solvent employed in the toxicant solution has been proven by field test not to be repellent to flies, and that any other appropriate solvent of like properties can be employed in its place.

Compositions in accordance with the invention as a class give excellent fly killing results when utilized in any area where flies congregate. This enhanced utility is believed to stem from the fact that a synergistic fly attractant action occurs through the use of yellow sugar-based granules in conjunction with dark, organic, meat-containing granules such as the exemplary fish food preparation described. Moreover, by virtue of the fact that the toxicants utilized are at least partially absorbed into the carrier base therefor, the arrestant and killing effects alluded to previously are amplified, and the toxicants do not exhibit a repellent tendency on flies. This feature also provides the compositions hereof with a high degree of resistance to moisture inactivation, permitting utilization of the compositions in outside areas around dairy barns or the like.

In field tests with the present fly killing compositions it has been demonstrated that the latter give considerably higher kills over extended periods of time than those of the prior art. It is also significant that the identical toxicants are employed in some of the prior compositions, as compared to those presently employed. Nevertheless, a significantly higher kill resulted with the instant compositions, thus confirming the synergistic effect thereof.

The flies killed in these tests were of many varieties, for example Musca domestica, Fannia, Phormia and Callephora. Additionally, a number of other insects such as ants, sowbugs and roaches can also be killed after adequate contact with the present composition.

It has also been found that the fly baits hereof are useable in virtually any area where flies congregate.

For example, the compositions can be spread in fly attracting disposition around dairy barns, poultry houses or other livestock pens to good effect. In this connection, it was determined that one-fourth pound quantity of the composition of the Example is adequate to effectively cover an area of about 500 square feet and protect the latter from flies for an extended period.

Having thus described the invention, what is claimed as new and desired to be secured by Letters Patent is:

1. A fly killing composition, comprising: from about 2 to 20% by weight, based upon the total weight of the composition, of a dark, organic, absortive granular component comprising:

| | |
|---|---|
| Beef Meal Scraps and By-Products | 15.00 – 20.00% |
| Dried Poultry By-Products | 10.00 – 15.00% |
| Cottonseed Meal | 15.00 – 20.00% |
| Soybean Meal | 10.00 – 15.00% |
| Pulverized Milo | 15.00 – 20.00% |
| Wheat Middlings | 1.00 – 5.00% |
| Dehydrated Alfalfa Meal | 10.00 – 15.00% | wherein all precentages immediately above are given on a weight basis and separately total 100%;

from about 70 to 90% by weight, based upon the total weight of the composition of a cooked yellow, sugar-based granular component comprising:

| | |
|---|---|
| Sugar | 40.00 – 60.00% |
| Corn Syrup | 10.00 – 15.00% |
| Corn Grits | 20.00 – 30.00% |
| Corn Cereal | 5.00 – 10.00% |
| Egg Yolk Powder | 0.01 – 0.10% |
| Milk Powder | 0.25 – 1.00% |
| Vegetable Oil | 1.00 – 5.00% |
| Yellow Food Grade Coloring | 0.15 – 0.50% | wherein all precentages immediately above are given on a weight basis and separately total 100%;

a toxicant mixture residing on the surface of said granular components and being at least partially absorbed into the interstices thereof, said toxicant mixture comprising from about 0.10 to 3.00% by weight 2,2-dichlorovinyl 0,0-dimethyl phosphate, based upon the total weight of the composition, and from about 0.25 to 2.00% by weight 0,0-dimethyl 0-2,4,5-trichlorophenylphosphorothioate, based upon the total weight of the composition; and a particulate coating mixture on said granular components and comprising from about 0 to 10% dried milk, from about 0–5% dried egg yolks, from about 0.1 to 5% hydrated amorphous silica oxide and yellow food dye in sufficient quantity to give the coating mixture a yellow color, all percentages being based on the total weight of the composition.

2. The fly killing composition of claim 1, wherein said 2,2-dichlorovinyl 0,0-dimethyl phosphate is employed in an amount of about 0.57% by weight and said 0,0-dimethyl 0-2,4,5-trichlorophenylphosphorothioate is employed in an amount of about 0.54% by weight, both based upon the total weight of the composition.

3. A method of killing flies which comprises placing in fly attracting disposition a composition which comprises:

from about 2 to 20% by weight, based upon the total weight of the composition, of a dark, organic, absortive granular component comprising:

| | |
|---|---|
| Beef Meal Scraps and By-Products | 15.00 – 20.00% |
| Dried Poultry By-Products | 10.00 – 15.00% |
| Cottonseed Meal | 15.00 – 20.00% |
| Soybean Meal | 10.00 – 15.00% |
| Pulverized Milo | 15.00 – 20.00% |
| Wheat Middlings | 1.00 – 5.00% |
| Dehydrated Alfalfa Meal | 10.00 – 15.00% | wherein all percentages immediately above are given on a weight basis and separately total 100%;

from about 70 to 90% by weight, based upon the total weight of the composition of a cooked yellow, sugar-based granular component comprising:

| | |
|---|---|
| Sugar | 40.00 – 60.00% |
| Corn Syrup | 10.00 – 15.00% |
| Corn Grits | 20.00 – 30.00% |
| Corn Cereal | 5.00 – 10.00% |
| Egg Yolk Powder | 0.01 – 0.10% |
| Milk Powder | 0.25 – 1.00% |
| Vegetable Oil | 1.00 – 5.00% |
| Yellow Food Grade Coloring | 0.15 – 0.50% | wherein all precentages immediately above are given on a weight basis and separately total 100%;

a toxicant mixture residing on the surface of said granular components and being at least partially absorbed into the interstices thereof, said toxicant mixture comprising from about 0.10 to 3.00% by weight 2,2-dichlorovinyl 0,0-dimethyl phosphate, based upon the total weight of the composition, and from about 0.25 to 2.00% by weight 0,0-dimethyl 0-2,4,5-trichlorophenylphosphorothioate, based upon the total weight of the composition; and a particulate coating mixture on said granular components and comprising from about 0 to 10% dried milk, from about 0–5% dried egg yolks, from about 0.1 to 5% hydrated amorphous silica oxide and yellow food dye in sufficient quantity to give the coating mixture a yellow color, all percentages being based on the total weight of the composition.

* * * * *